US006894784B2

(12) United States Patent
Simon, Jr. et al.

(10) Patent No.: US 6,894,784 B2
(45) Date of Patent: May 17, 2005

(54) FOAM DETECTOR AND DISRUPTOR

(75) Inventors: Richard K. Simon, Jr., College Station, TX (US); Nathan C. Rawls, College Station, TX (US)

(73) Assignee: O. I. Corporation, Inc., College Station, TX (US)

( * ) Notice: Subject to any disclaimer, the term of this patent is extended or adjusted under 35 U.S.C. 154(b) by 223 days.

(21) Appl. No.: 10/288,391

(22) Filed: Nov. 5, 2002

(65) Prior Publication Data

US 2004/0083892 A1 May 6, 2004

(51) Int. Cl.⁷ .......................... G01N 21/00; B01D 53/14
(52) U.S. Cl. ........................................ 356/432; 96/102
(58) Field of Search ............................ 356/432; 96/102

(56) References Cited

U.S. PATENT DOCUMENTS

2002/0088823 A1 * 7/2002 Tabacchi et al. ............... 222/52

FOREIGN PATENT DOCUMENTS

WO    WO 01/69264 A1    9/2001    .......... G01N/37/00

* cited by examiner

Primary Examiner—Zandra V. Smith
(74) Attorney, Agent, or Firm—Wong, Cabello, Lutsch, Rutherford & Brucculeri, LLP

(57) ABSTRACT

An apparatus and method are disclosed to detect foam above a liquid sample in a sparge vessel, and disrupt any foam that may exist. The foam sensor includes an optical emitter and optical sensor coupled to a sparge vessel above the level of the liquid sample. Foam is detected if the light beam is attenuated or blocked. The foam disrupter provides thermal energy to raise the temperature of a surface in the sparge vessel to break up the foam, which may condense on the walls of the sparge vessel.

20 Claims, 5 Drawing Sheets

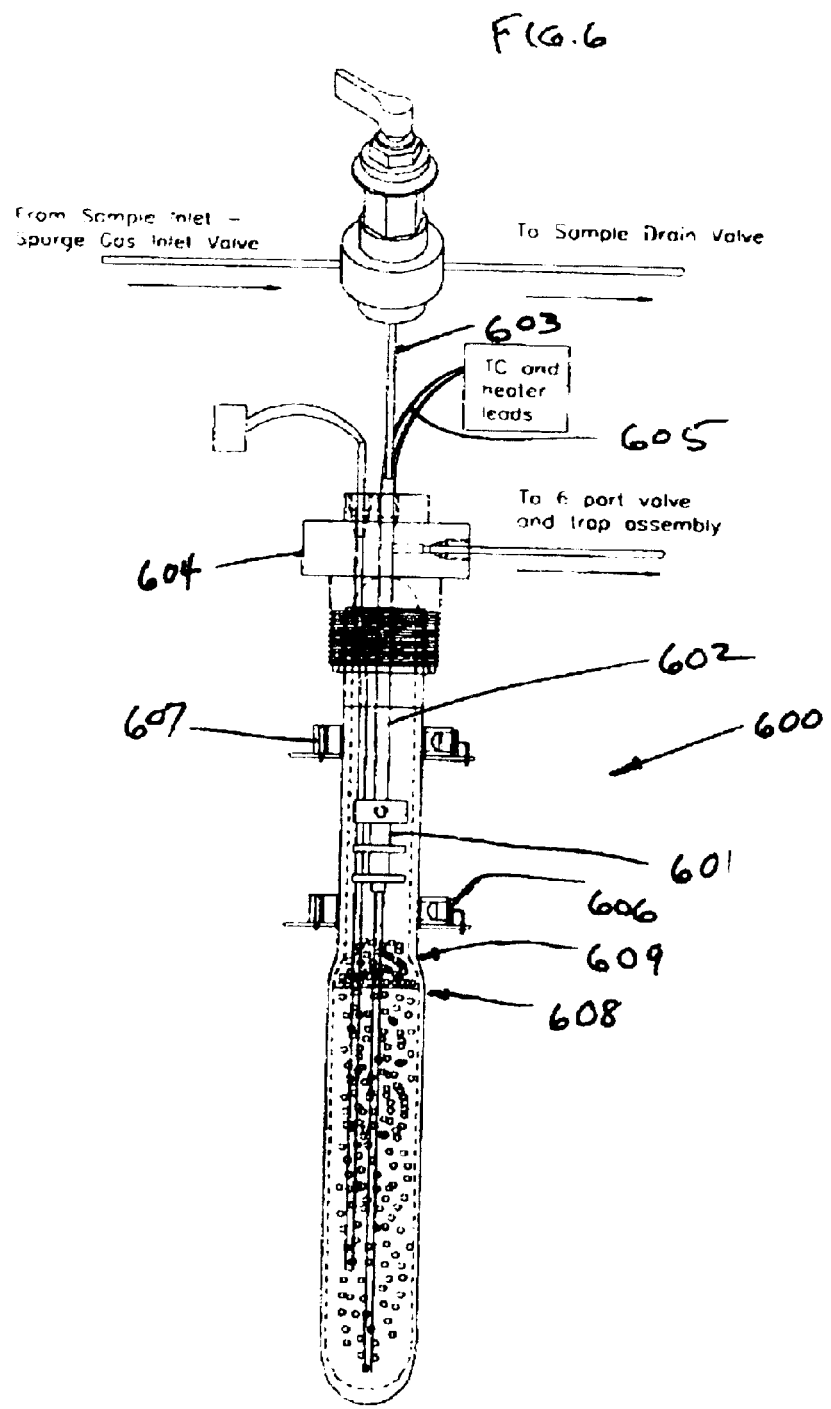

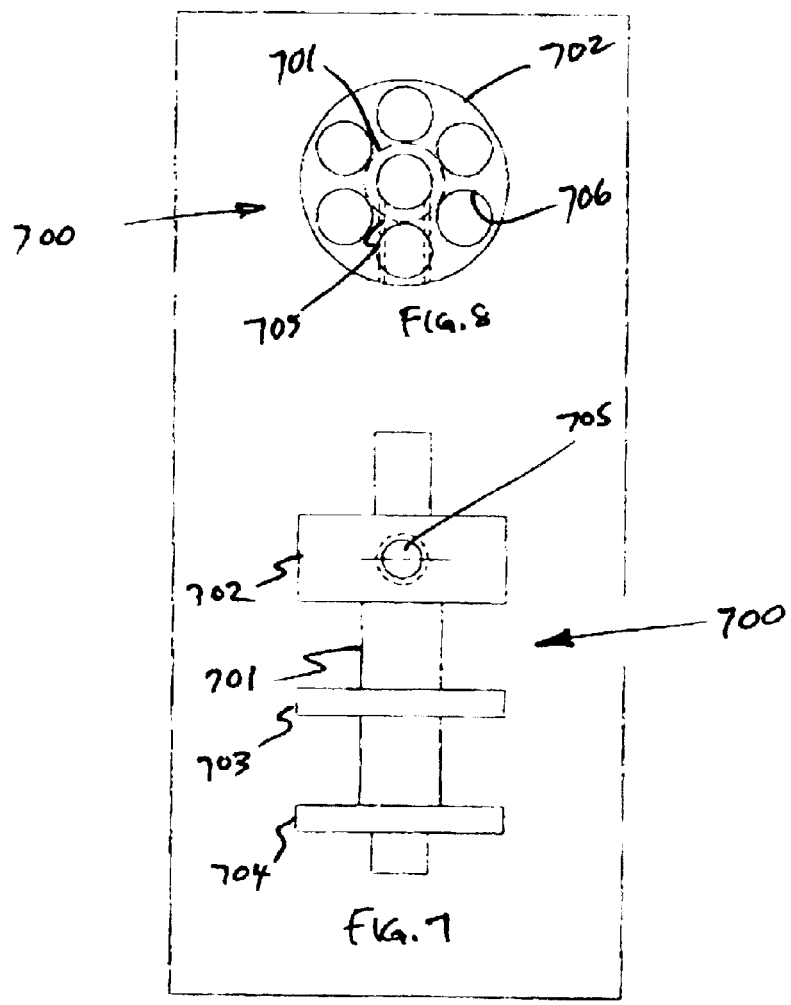
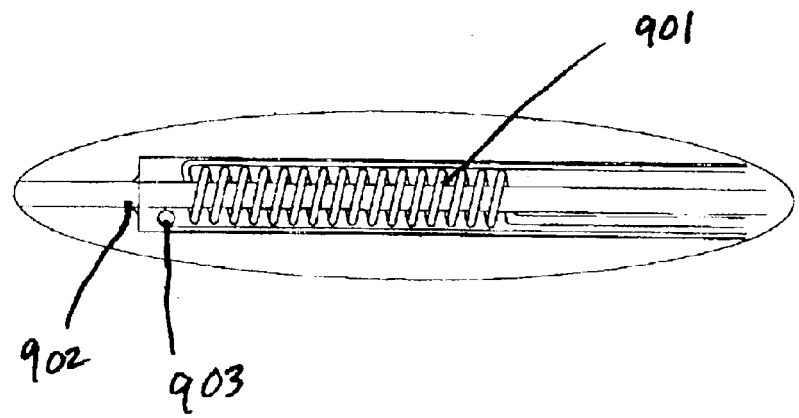

FOAM DETECTOR AND DISRUPTOR

BACKGROUND

This invention relates to sample concentration for gas chromatography and specifically to inhibition of foam in samples that are concentrated and analyzed using gas chromatography techniques.

A purge and trap sample concentrator is a device that may be used to extract volatile and semi-volatile analytes from a sample by passing a purge gas through the sample and trapping analytes onto a sorbent bed or trap. Subsequent desorption from the trap, and transfer of the desorbed analytes to a gas chromatograph, allows for separation and quantitative analysis of the volatile analytes.

One problem in the extraction process is that some samples have a tendency to form a foam which, if unabated, can be transferred throughout the purge and trap system, and may contaminate the entire system and require the entire system to be serviced, cleaned, revalidated, and/or calibrated.

One approach to this problem is pre-treating suspect samples with de-foaming solutions such as polypropylene glycol 2000, or Dow Corning Silicone RID emulsion.

However, this pre-treating can alter the extraction process itself, raising concerns regarding sample integrity, particularly for analytes that are highly volatile.

A purge and trap sample concentrator includes a sparge vessel in which an aliquot of a sample is placed. A first type of sparge vessel has a generally U-shaped tube, with a frit installed in a first leg or side of the U-shaped tube. A sample may be introduced into the first leg or side of the sparge vessel having the frit. Couplings may be attached to each side of the sparge vessel to create a sealed system. The output coupling is attached to the leg or side of the sparge vessel having a frit. The output coupling may contain a valve and needle assembly, a port, and additional components such as temperature sensors. The valve and needle assembly are for sample introduction and removal (draining). The port is to direct the purged analytes from the sample through tubing to the sorbent bed or trap.

A second type of sparge vessel, often referred to as a needle sparge assembly, has a sealed tube with a valve and needle that serves as a sample inlet, sparge flow inlet, and drain tube. Sparge gas is passed through the needle to generate bubbles and sparge the sample of the volatile and semi-volatile analytes.

Purging analytes from either type of sparge vessel may result in foam. The action of the frit in the first type of sparge vessel is to generate small gas bubbles across the top of the frit. In the needle sparge assembly, the gas that elutes from the needle generates bubbles. The small bubbles enhance the extraction efficiency of the gas passing through the sample. However, a potential side effect of this aeration process is the formation of foam. Generally, bubbles rupture at the liquid interface at the top of the sample. However, some samples retain the bubbles as an aggregate (foam) and this aggregate may be transported throughout the sample concentrator system. This may contaminate the system and necessitate cleaning.

Various designs of sparge vessels have been made to reduce the propensity for foam propagation. For example, for large volume bubbles, expanding the diameter of the sparge vessel (above the air-liquid interface) may help the bubbles rupture due to expansion forces becoming greater than the surface tension of the bubble. For highly viscous samples, a mud-dawger, which is a pointed element on a needle or other structural element in the sparge vessel, may be used to rupture the bubbles. However, these solutions are especially ineffective for small bubbles that flow around or through the potential mechanical foam disruption elements.

Other attempts have been made to detect foam in a sparge vessel. For example, WO 01/69264 discloses a conductivity sensor within a sparge vessel for the detection of foam. The conductivity sensor provides an alarm when foam is detected, permitting the user to dispose of the sample without continued analysis. The device in WO 01/69264 may detect foam without eliminating or reducing the foam. Also, the conductivity sensor may not detect foam that is not conductive.

Thus, a device and method are needed to detect, reduce and/or eliminate foam that is in sparge vessels in purge and trap sample concentrators.

BRIEF DESCRIPTION OF THE DRAWINGS

FIG. 6 is a cross section view of a sparge vessel with a pair of foam detectors and an internal foam disrupter according to one embodiment of the invention.

FIG. 7 is a side view of an internal foam disrupter according to one embodiment of the invention.

FIG. 8 is a top view of an internal foam disrupter according to one embodiment of the invention.

FIG. 9 is a partial section view of a foam disrupter according to one embodiment of the invention.

DETAILED DESCRIPTION

Figure 1:
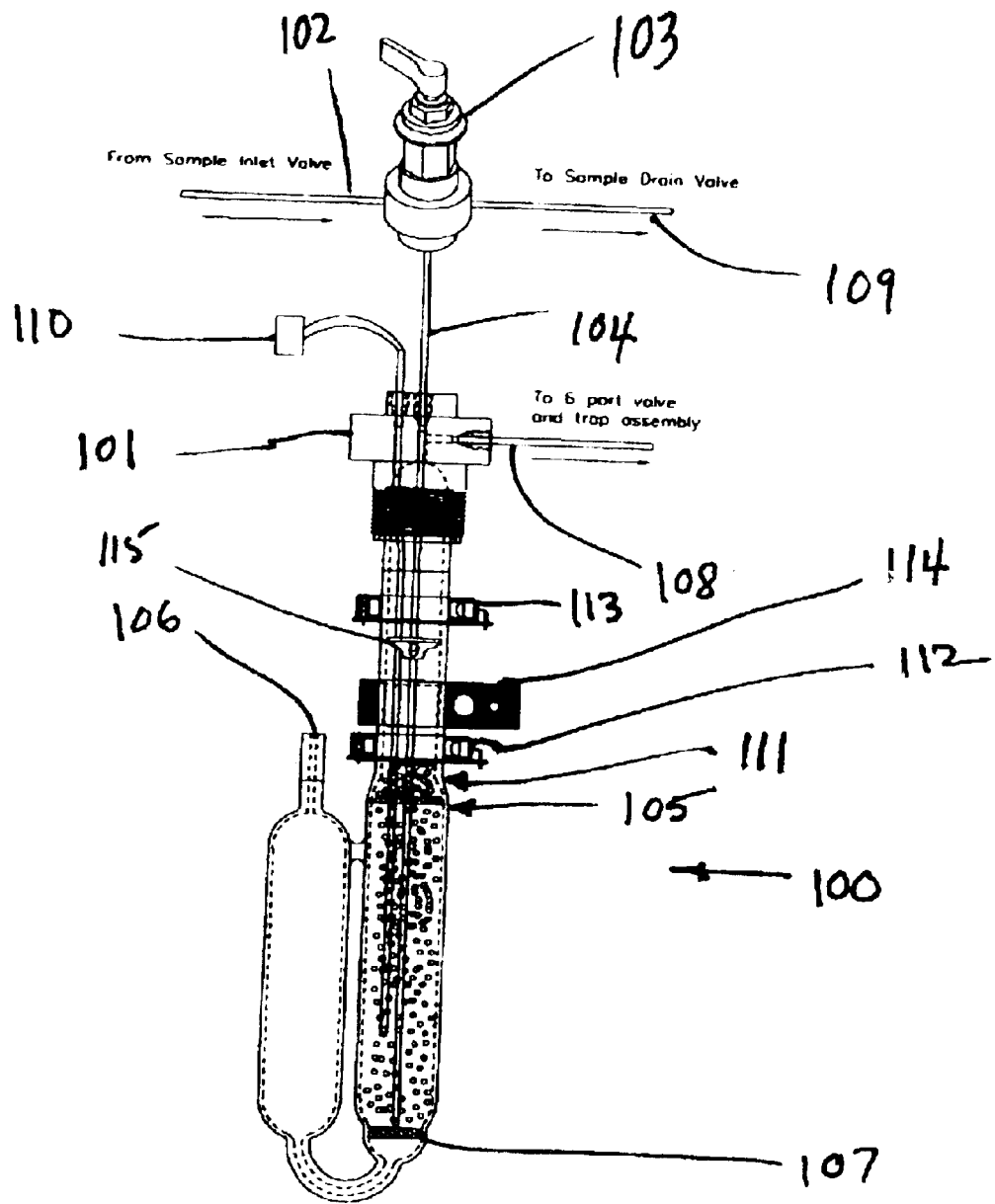
FIG. 1 is a cross section view of a U-shaped sparge vessel with a pair of foam detectors, an external foam disrupter and droplet diverter according to one embodiment of the invention.

FIG. 1 shows sparge vessel 100 which may be a U-shaped tube that holds a liquid sample to be purged. Coupling 101 may be mounted on one end of the sparge vessel to seal the sparge vessel and to provide one or more passages or ports through which lines or conduits access the interior of the sparge vessel. A liquid sample may enter the sparge vessel through inlet line 102, valve 103, and line 104. The volume of the liquid sample in the sparge vessel is indicated by liquid level 105. Purge gas may enter the sparge vessel through purge gas inlet 106, forming small bubbles when passing through frit 107, and flowing through the liquid sample to purge analytes from the liquid sample. Analytes purged from the liquid sample flow through outlet line 108 to a sorbent trap (not shown). A multi-port valve also may be included in outlet line 108 to control the flow of purged analytes to the trap. After purging, the liquid sample may be drained through outlet line 109 to a sample drain valve. Temperature sensor 110 may be used to maintain the sparge vessel at an appropriate temperature, i.e., ambient temperature or in the range of approximately 40 to 80 degrees Centigrade.

Before and/or during purging of analytes from the sample, foam 111 may be generated above the liquid level. In one embodiment of the invention, one or more foam detectors 112, 113 are used to detect foam above liquid level 105. According to this embodiment, the foam detector includes an optical emitter that provides a light beam and an optical sensor coupled to the emitter to detect the light beam unless the light beam is attenuated, disrupted or blocked by foam above the liquid level of the sample. The optical emitter may provide light at a visible or non-visible spectrum, or may provide light pulses at a specified frequency. The optical sensor detects the light pulses at the transmitted spectrum and/or frequency.

In the embodiment of FIG. 1, the foam detector(s) may be mounted or coupled to the outside or external surface of the sparge vessel. In this embodiment, the light beam or light pulses may be transmitted through the transparent surface of the sparge vessel. Alternatively, the foam detector may be mounted inside the sparge vessel.

In one embodiment of the invention, detection of excess foam above the sample may cause one or more of the following actions: (1) the sample may be drained from the sparge vessel; (2) a signal generator may activate an alarm message or other signal; (3) purge gas flow through the sample may be halted; (4) purge gas flow through the sample may be reduced; and/or (5) purge gas flow may be directed to a back flush vent.

In one embodiment of the invention, one or more foam disruptors break up and disrupt the foam above the sample. In the embodiment of FIG. 1, foam disrupter 114 is a heated element that provides thermal energy to a surface in the sparge vessel to burst the foam bubbles due to gas expansion and/or vaporization. The foam disrupter may be mounted or positioned above the liquid level of the sample in the sparge vessel. In the embodiment of FIG. 1, the foam disrupter is positioned between foam detector 112 and foam detector 113. The foam disrupter may be activated before and/or during purging of analytes from the sample, or may be activated only when foam is detected above the sample by a foam sensor that detects the foam optically or by conductivity.

To break up the foam, the foam disrupter may provide thermal energy to vaporize the foam by raising the temperature in the heated region of a surface in the sparge vessel above the liquid level. The temperature of the surface may be raised over the boiling point of the sample. When the foam contacts the heated surface, the foam vaporizes, and the vapor may rise above the heated region of the sparge vessel, condense on the walls of the sparge vessel, and drain back into the sample liquid. The temperature of the heated surface of the foam disruptor may be in the range of 100 to 200 degrees Centigrade. In one embodiment of the invention, a temperature sensor coupled to the foam disrupter may be used to monitor and/or aid in control of the temperature of the foam disrupter.

In the embodiment of FIG. 1, foam disrupter 114 is mounted or coupled to the external or outside surface of the sparge vessel. In this embodiment, the foam disrupter is a heated aluminum block and the heated surface that comes into contact with foam is the internal wall of the sparge vessel above the liquid level.

In accordance with the present invention, other heating elements also may be used to disrupt foam, and may be mounted or coupled to the exterior wall of the-sparge vessel above the liquid level of the sample. The choice of the heater element includes cartridge, kapton, tape, band, strip, polymer thick film, coil, heater wire, etc. and may utilize a temperature sensor such as a thermocouple, thermistor, or platinum resistance thermometer.

In one embodiment of the invention, the foam disrupter may run at full power with the heating assembly providing adequate power to heat the interior wall of the sparge vessel to a high enough temperature to rupture the foam as the foam makes contact with the region of the sparge vessel above the liquid sample which is being heated. Alternatively, in another embodiment of the invention, the foam disrupter may be actively controlled by a thermal sensor.

One embodiment of the invention may include a processor, control circuitry and/or control program to operate and activate the foam detector, operate and select a temperature for the foam disrupter, energize valves associated with the sparge vessel, and specify the desired action or actions if foam is detected. For example, if the foam detector senses excess foam in the sparge vessel, an alarm message or signal may be generated and sent to the control circuitry to energize the appropriate valves to drain the sample from the sparge vessel. Similarly, an alarm message or signal may be generated and sent to the control circuitry to halt air purge, and/or open back flush valves to direct the purge gas flow to a back flush vent rather than the line to the sorbent trap. The backflush valve may also be used to direct air or other media into the backflush vent and clean one or more lines between the backflush vent and the sparge vessel, i.e. those lines upstream of the trap. Alternatively, detection of excess foam by the foam detector may be used to decrease the flow of purge gas through the sample.

If two or more foam detectors are used, each detector may provide the same or a different action if foam is detected. For example, one of the foam detectors (i.e., foam detector 112) may send a message to the control circuitry that a sample is foaming, and the control circuitry may send a message to the control program which logs that the sample foamed. The other foam detector may provide signals to drain the sample, redirect purge gas flow, or reduce the purge gas flow rate until the foam disrupter element can effectively vaporize the foam, and when the foam has been reduced, reset the flow rate of the purge gas back to its normal flow rate.

Figure 2:
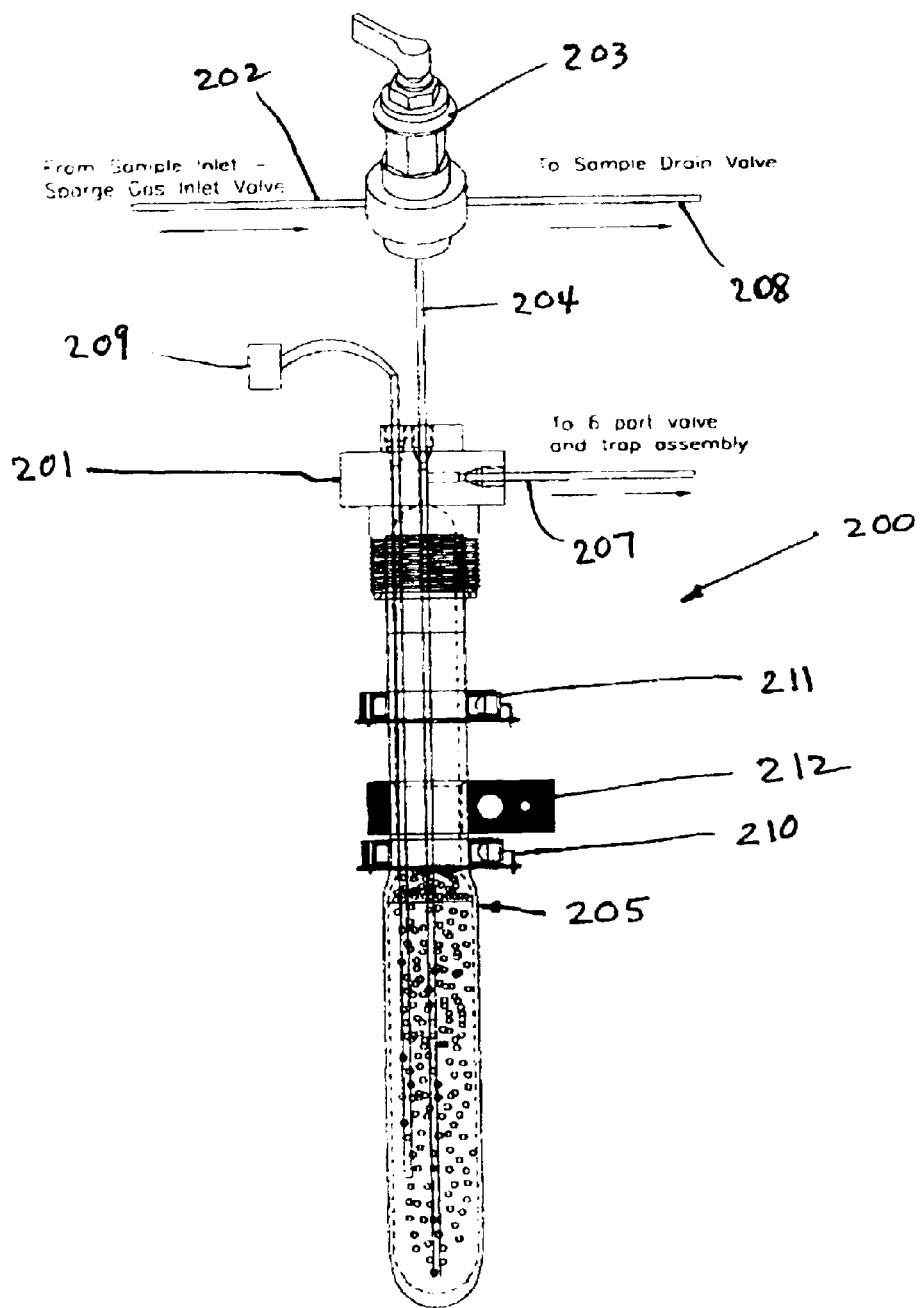
FIG. 2 is a cross section view of a sparge vessel with a pair of foam detectors and an external foam disrupter according to one embodiment of the invention.

In FIG. 2, sparge vessel 200 holds a liquid sample to be purged. Coupling 201 may be mounted on one end of the sparge vessel to seal the sparge vessel and provides passages or ports through which lines or conduits access the sparge vessel. A liquid sample may enter the sparge vessel through inlet line 202, valve 203, and line 204. The volume of the liquid sample is indicated by liquid level 205. Line 204 also serves as the purge gas inlet for purge gas to bubble through the liquid sample to purge analytes from the liquid sample. Analytes purged from the sample flow through outlet line 207 to a sorbent trap (not shown). A multi-port valve also may be included in outlet line 207 to control the flow of purged analytes to the trap. After purging, the liquid sample may be drained through outlet line 208 to a sample drain valve. Temperature sensor 209 may be used to maintain the sparge vessel at an appropriate temperature, i.e., ambient temperature or in the range of approximately 40 to 80 degrees Centigrade.

Foam detectors 210, 211 shown in FIG. 2 may detect foam above liquid level 205 using a light emitter and a light sensor that detects a light beam or light pulses unless it is attenuated by foam above the liquid level of the sample. In the embodiment of FIG. 2, foam disrupter 212 is a heated element that provides thermal energy to burst the foam bubbles due to gas expansion and/or vaporization of the foam. The foam disrupter may be mounted or positioned above the liquid level of the sample in the sparge vessel, and/or may be mounted to the external or outside surface of the sparge vessel.

Figure 3:
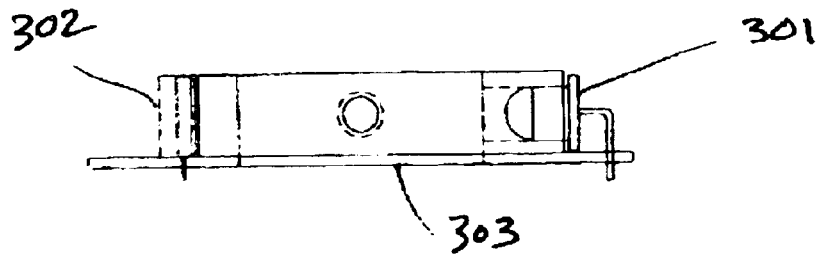
FIG. 3 is a side view of a foam detector according to an embodiment of the invention.

FIG. 3 shows an embodiment of the foam detector used in FIGS. 1 and 2. This foam detector includes optical emitter 301 that provides a light beam directed at light sensor 302. For example, the foam detector may be a Hamamatsu model L1915-01 IR emitter with lens window, and a Hamamatsu model S4282-51 IC light module, mounted to circuit board 303.

As discussed above, foam that is vaporized by the foam disrupter may condense on the sides or interior walls of the sparge vessel and drain into the liquid sample. If the walls of the sparge vessel are heated, however, the condensed foam on the walls of the sparge vessel may vaporize again.

Optionally, as shown in FIG. 1, in one embodiment of the invention, droplet diverter 115 may be mounted in the sparge vessel above the foam disrupter to direct condensation on the interior side walls of the sparge vessel to flow to lower temperature regions near the center of the sparge vessel. Thus, the droplet diverter may help prevent revaporization of foam. One or more droplet diverters may be used in embodiments of the present invention.

Figure 4:
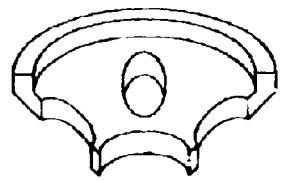
FIG. 4 is a top view of a droplet diverter according to one embodiment of the invention.
Figure 5:
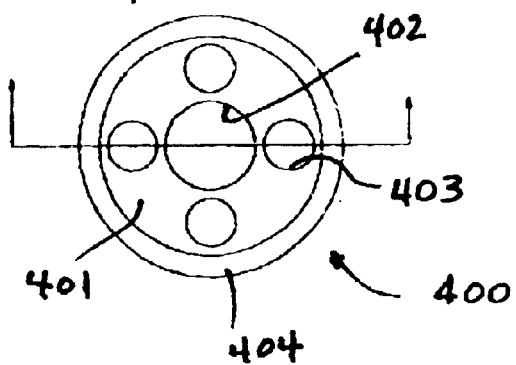
FIG. 5 is a side view of a droplet diverter according to one embodiment of the invention.
Figure 5:
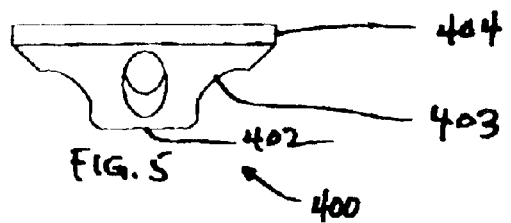

As shown in FIG. 4 and FIG. 5, in one embodiment, droplet diverter 400 may be a generally dish-shaped element having a sloped or concave upper surface 401, a central passage 402 through which a line may extend, and one or more apertures or holes 403 in the lower surface thereof. The apertures help ensure gas flow through the droplet diverter and allow thermocouples, inlet/outlet needle assemblies, and the like to be routed through the droplet diverter. The droplet diverter may be made from glass, metal, ceramic, or plastic, or other materials that are inert relative to the sample matrix in the sparge vessel. The droplet diverter should not absorb the analytes of interest, nor should it prevent flow of the sparge gas through the sparge vessel. The droplet diverter may be bonded, fused, or pinned to the sparge vessel, or may be attached to a shoulder or ledge in the sparge vessel. Alternatively, the droplet diverter may be integral with the sparge vessel. For example, a droplet diverter integral with the sparge vessel may include a series of angled internal dimples.

FIG. 6 shows an embodiment of the invention in which foam disrupter 601 is mounted inside sparge vessel 600. The foam disrupter may be mounted or coupled to sleeve 602 that at least partially covers inlet line 603 extending through coupling 604 mounted to the sparge vessel. Thermocouple and heater leads 605 also may be routed through the sleeve. This foam disrupter heats a thermal element in the sparge vessel rather than the walls of the sparge vessel, so droplets that condense on the walls of the sparge vessel may flow back into the sample liquid. Also shown are foam detectors 606, 607, both of which are mounted above liquid level 608 to detect foam 609. The foam disrupter of FIG. 6 also may be included in a U-shaped sparge vessel.

FIGS. 7 and 8 show the foam disrupter of FIG. 6 in more detail. Foam disrupter 700 may include a cylindrical heater cartridge body 701 with radiator having fins 702, 703, 704 that extend radially from the heater cartridge body to provide heated surfaces which disrupt and break up the foam. Set screw 705 may connect the radiator part of the foam disrupter to a heating element that optionally may include a thermal sensor. The fins may have holes or apertures 706 so that one or more tubes, lines and/or temperature sensing elements may extend therethrough and provide additional pathways to force the foam to make contact with the foam disrupter, yet minimize back restriction to the gas flow through the sparge vessel.

In one embodiment of the invention, a control circuit may be included to detect and maintain a desired temperature at or near the base of the foam disrupter. The control circuit may be configured to keep the sensor region at a constant temperature. Foam that breaks up at or near the base of the foam disrupter will extract energy and cool the base, dropping its temperature. As a result, additional power may be provided to the foam disrupter when more foam is present, and the upper section of the foam disrupter may be heated to a higher temperature relative to the base region. Foam that moves above the base region of the heated element enters into a region of higher temperature and greater thermal mass. The thermal gradient and greater thermal mass enhances the capacity of the foam disrupter to break up foam. Thus, the control circuit may provide greater power when foam is present and lower power when foam is not present.

In one embodiment, monitoring of the power level and/or temperature of the foam disrupter may be used to detect the presence of foam, and thus also serve as a foam sensor. When foam is sensed, the control circuit may set an alarm, send the sample to drain, divert gas flow from the sparge vessel, decrease the flow rate through the sparge vessel (to decrease the rate of foam production), or any combination of the above. Monitoring of the power level and temperature of the foam disrupter permits measurement of the rate of foam generation, and allows the user to take action to decrease the rate of foam production, or to simply discharge the sample to drain to prevent contamination of the purge and trap sample concentrator.

FIG. 9 shows an embodiment of the invention in which the heating element, temperature sensor and drain tube may be made as a single assembly. In this embodiment, the heating element 901 is a coil around tubing 902. A thermocouple 903 also may be included to control the temperature of the heating element.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An apparatus comprising:

a sparge vessel to hold a liquid sample;

a light emitter to direct a light beam through a portion of the sparge vessel above the liquid sample; and a light detector coupled to the light emitter to detect the light beam.

2. The apparatus of claim 1 wherein the light emitter directs pulses of light through the sparge vessel.

3. The apparatus of claim 1 wherein the light emitter is mounted on the sparge vessel.

4. The apparatus of claim 1 wherein the light emitter and light detector are-mounted on the sparge vessel.

5. The apparatus of claim 1 further comprising a signal generator coupled to the light detector, the light detector activating the signal generator if the light beam is not detected.

6. The apparatus of claim 1 further comprising a heated element to heat a surface above the liquid sample.

7. The apparatus of claim 6 wherein the foam disrupter is mounted on the sparge vessel.

8. The apparatus of claim 6 wherein the foam disrupter is inside the sparge vessel.

9. An apparatus comprising:
   a sparge vessel to hold a liquid sample, the sparge vessel having an inlet through which purge gas flows into the liquid sample, and an outlet through which analytes purged from the liquid sample exit the sparge vessel; and
   a foam disrupter coupled to the sparge vessel above the liquid sample, the foam disrupter generating thermal energy to raise the temperature of a surface in the sparge vessel to at least the boiling point of the liquid sample.

10. The apparatus of claim 9 wherein the foam disruptor is mounted on the exterior of the sparge vessel.

11. The apparatus of claim 9 wherein the foam disrupter is mounted inside the sparge vessel.

12. The apparatus of claim 9 further comprising a temperature sensor coupled to the foam detector.

13. The apparatus of claim 9 further comprising a droplet diverter in the sparge vessel to direct condensed foam inwardly.

14. The apparatus of claim 9 further comprising at least one foam detector coupled to the sparge vessel.

15. A method comprising:
   emitting a light beam through a sparge vessel above a liquid sample level in the sparge vessel;
   sensing the light beam to determine if foam exists above the liquid sample level; and
   heating a surface in the sparge vessel above the liquid sample level to break up foam that may exist.

16. The method of claim 15 further comprising directing condensation inwardly from the sparge vessel.

17. The method of claim 15 further comprising emitting a pulsed light beam.

18. The method of claim 15 further comprising emitting a first light beam and a second light beam above the liquid sample level, and sensing the first and second light beams.

19. The method of claim 15 further comprising heating a portion of the outer surface of the sparge vessel to a temperature at least as high as the boiling point of the liquid sample.

20. The method of claim 15 further comprising heating a surface inside the sparge vessel above the liquid sample level to a temperature at least as high as the boiling point of the liquid sample.

* * * * *